(12) United States Patent
Baragar et al.

(10) Patent No.: US 6,282,728 B1
(45) Date of Patent: Sep. 4, 2001

(54) GOGGLES WITH DUAL LENS STRUCTURE

(75) Inventors: Marc C. Baragar; Bruce F. Milton, both of Vancouver (CA)

(73) Assignee: Xenophon Design Inc., Vancouver (CA)

( * ) Notice: Subject to any disclaimer, the term of this patent is extended or adjusted under 35 U.S.C. 154(b) by 0 days.

(21) Appl. No.: 09/597,498

(22) Filed: Jun. 19, 2000

(30) Foreign Application Priority Data

Jan. 19, 2000 (CA) .................................................. 2296267

(51) Int. Cl.⁷ ....................................................... A61F 9/02
(52) U.S. Cl. .................................................. 2/428; 351/43
(58) Field of Search .......................... 2/428, 430; 351/43

(56) References Cited

U.S. PATENT DOCUMENTS

| | | | |
|---|---|---|---|
| 2,317,658 | 4/1943 | Welsh . | |
| 3,015,987 | * 1/1962 | Harrison | 351/43 |
| 3,040,616 | 6/1962 | Simpson . | |
| 4,317,240 | 3/1982 | Angerman et al. . | |
| 4,373,788 | * 2/1983 | Herbert | 351/43 |
| 5,313,671 | * 5/1994 | Flory | 2/428 |
| 5,420,649 | * 5/1995 | Lewis | 351/43 |
| 5,896,589 | * 4/1999 | Chou | 2/428 |
| 6,115,848 | * 9/2000 | Key | 2/428 |
| 6,158,859 | * 12/2000 | Suiter | 351/43 |

* cited by examiner

*Primary Examiner*—John J. Calvert
*Assistant Examiner*—Katherine Moran
(74) *Attorney, Agent, or Firm*—Townsend and Townsend and Crew LLP (57) ABSTRACT

Goggles having a transparent body adapted to be worn over the eyes and including anterior and posterior lenses spaced apart to permit fluid flow therebetween. The anterior lens is shaped so as to reduce fluid drag and the posterior lens is shaped to minimize visual distortion.

23 Claims, 9 Drawing Sheets

Refraction of Light – Convex Lens $d = t \sin i \, (1 - 1/n)$ (d) displacement (r) angle of refraction (n) index of refraction (t) thickness (i) angle of incidence

GOGGLES WITH DUAL LENS STRUCTURE

BACKGROUND OF THE INVENTION

1. Field of the Invention

The present invention relates to goggles. More particularly, the present invention relates to goggles having a dual lens structure for use in recreational activities.

2. Description of Related Art

Eye protection adapted for recreational activities are well known and widely used to protect the eye from impact damage or visual disturbances caused by air or water flow directed toward the eye. In contrast to eyepieces that are used to correct vision defects, recreational goggles are routinely used in applications that require protection of the eye.

Conventionally, eye wear for recreational use is held in place adjacent the eye by a combined headband that extends about the rear of the head, a nosepiece that extends across the nose, and in the case of swim goggles, suction cups that fit and seal over the eye sockets. A pair of lenses in the eyepiece are positioned over the eyes to allow the user to substantially distortion free vision while protecting the eye from environmental irritants such as particulate matter, and air and water flow.

The lens that produces distortion free vision tends to be a planar lens that offers high resistance (high drag) to fluid flow past the lens. Conversely, a lens that is shaped for low drag tends to distort the image transmitted to the eye. There exist applications, such as swimming, where it is desirable for a lens to minimize visual distortion while at the same time minimizing drag.

The inventors are aware of patents that disclose devices which cooperate with a human face to reduce visual distortion due to light refraction across various media.

U.S. Pat. No. 3,040,616 (Simpson) discloses underwater goggles that are intended to address the problem of visual distortion underwater. The goggles are formed with recesses that allow water to flow between a flat window that is adjacent to the wearer's eyes and a curved rear lens. This patent relies on a pair of outer lenses separated from the inner lens by an air pocket to present an undistorted image to the wearer.

U.S. Pat. No. 2,317,658 (Welsh) discloses swimming goggles that have two spaced lenses. The space between the lenses, however, is not exposed to water.

U.S. Pat. No. 4,317,240 (Angerman et al.) discloses a pair of sports goggles that have a slot at the top portion of a lens for assisting air flow to pass between the lens to prevent fogging.

The lenses and seals of conventional swim goggles generally comprise a single relatively planar lens (to minimize visual distortion) mounted to a sealing member for engagement about the eye socket of a wearer. These swim goggles tend to rely on an interference fit between the seal and the face to produce an air pocket between the eye and the lenses. Of course, the generally flat lenses of conventional swim goggles are not streamlined resulting in increased hydro-dynamic drag. To reduce hydro-dynamic drag, it is necessary to increase the curvature of the lens, however, a curved lens tends to increase visual distortion and many users are not prepared to sacrifice clarity of vision for lower drag. The design considerations of minimal visual distortion and minimal drag are at odds with each other and to date users have had to sacrifice one in order to enjoy the other.

SUMMARY OF THE INVENTION

The present invention addresses the difficulties and disadvantages of the prior art by providing a simple goggle arrangement that has hydro-dynamic characteristics while still providing the same optical clarity of conventional goggles. The goggles can be manufactured using conventional plastic injection dye technology for a relatively low cost. The goggles provide conventional attachment means to secure the goggles to a human face to provide an air pocket between the eye and the goggles.

Accordingly, the present invention provides goggles for use in a fluid environment comprising a transparent body adapted to be worn over the eyes having anterior and posterior portions spaced apart to permit fluid flow therebetween, the anterior body portion being shaped so as to reduce fluid drag, and the posterior body portion being shaped to reduce visual distortion In a further aspect, the present invention provides swim goggles comprising:

(a) a pair of transparent eye pieces adapted to be worn over the eyes, each eyepiece having anterior and posterior portions spaced apart to permit fluid flow therebetween, the anterior portion being shaped so as to reduce fluid drag, the posterior portion being shaped to reduce visual distortion; and (b) a headband and a nosepiece attached to the eyepieces, the headband being of sufficient size to secure the swim goggles to a human head adjacent the eyes, the nosepiece being of sufficient size to secure the eyepieces over the nose.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
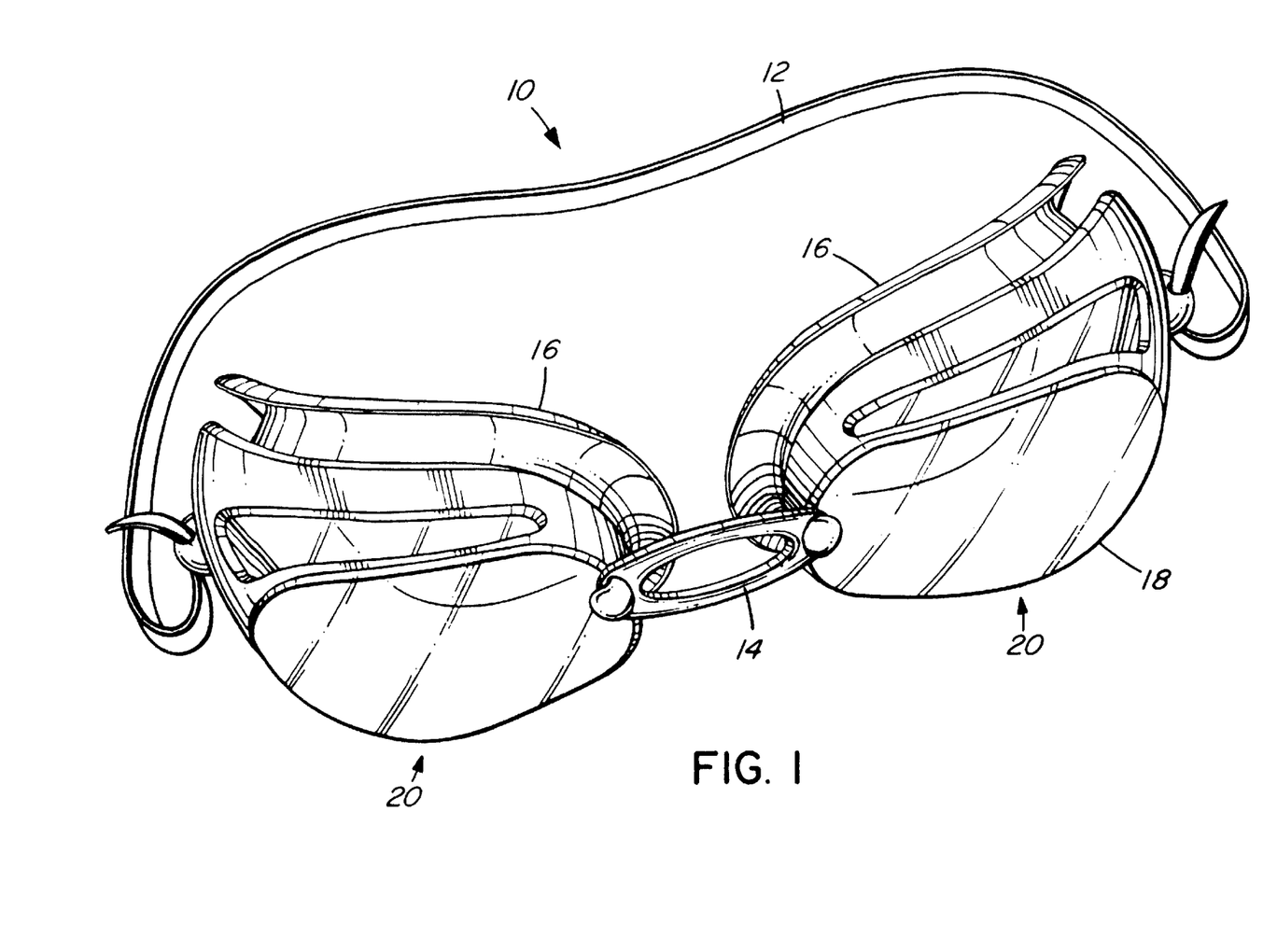
FIG. 1 is a perspective view of a first embodiment of the invention.
Figure 2A:
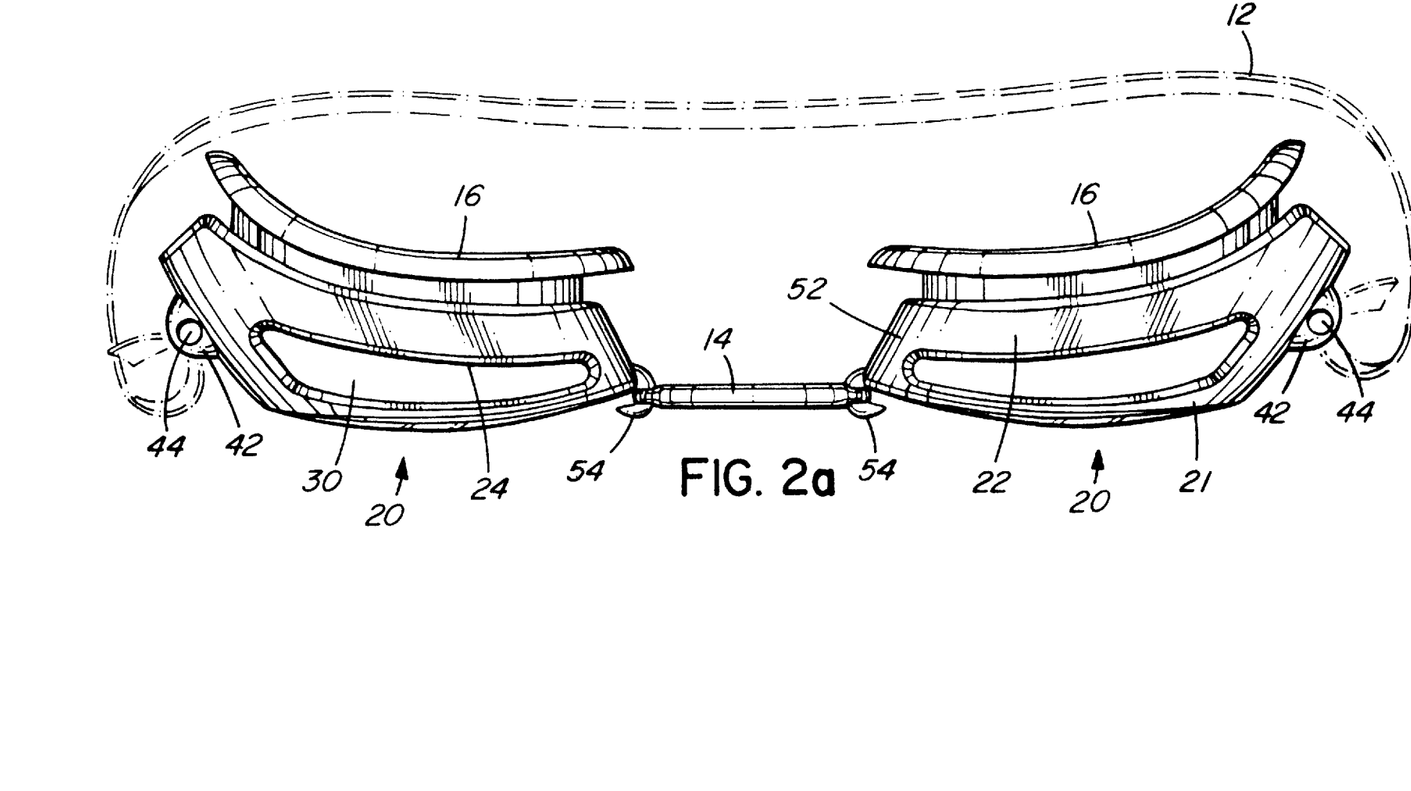
FIG. 2a is a top elevation view of the first embodiment in FIG. 1 showing a pair of transparent eyepieces.
Figure 2B:
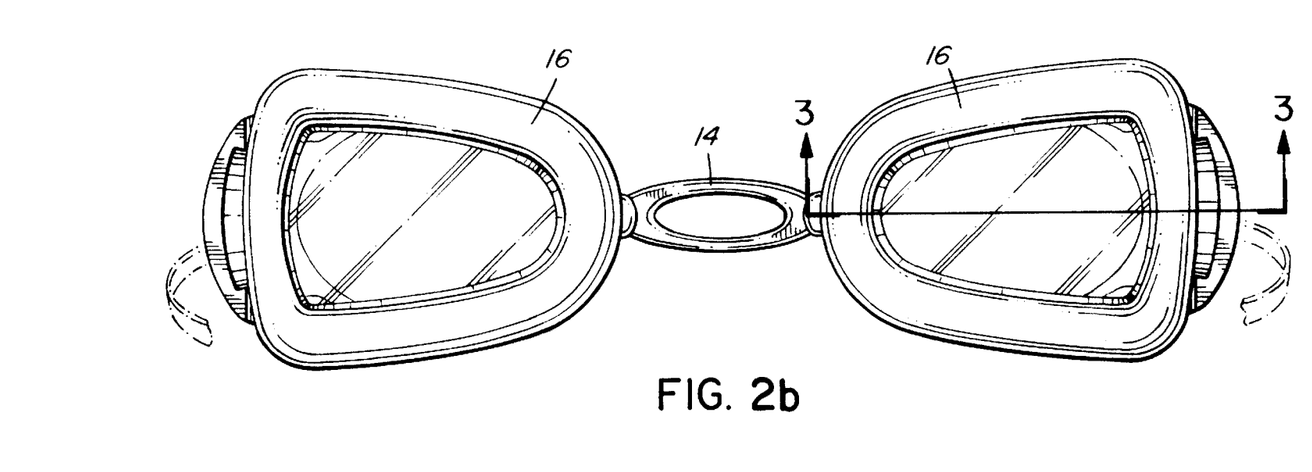
FIG. 2b is a rear elevation view of the first embodiment of FIG. 1.
Figure 2C:
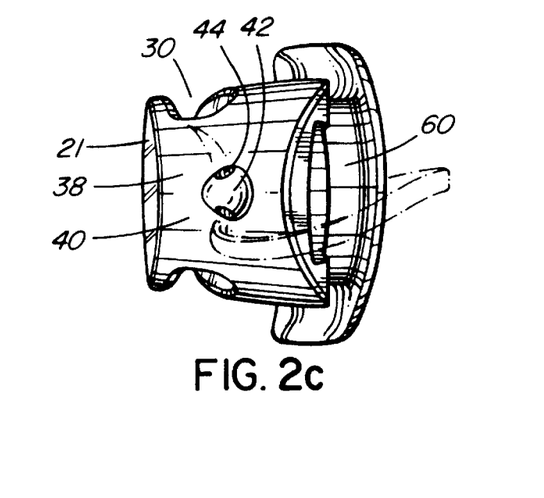
FIG. 2c is a side elevation view of the first embodiment of FIG. 1 showing a surface with reduced hydrodynamic drag.

Referring to FIGS. 1 and 2, a pair of goggles according to a first embodiment of the invention are shown generally at 10. The goggles 10 are shown with a conventional elasticated headband 12, a nosepiece 14 and a pair of seals 16 adapted to fit and seal over the eyes.

Goggles 10 are designed for use in a fluid environment to reduce visual distortion. The goggles include a transparent portion 18 adapted to be worn over the eyes. The transparent portions 18 comprise a pair of eyepieces 20 each having anterior and posterior eyepiece portions 21 and 22,respectively, as best shown in FIGS. 2a to 2c. As each eyepiece is essentially identical, only one will be described in detail. The anterior eyepiece portion 21 is shaped so as to reduce fluid drag. The posterior body eyepiece portion 22 has a substantially planar surface 24 for reducing visual distortion. The posterior portion 22 is of sufficient size and shape to substantially enclose the eye socket. In conventional sporting activities, the fluid may be, but is not restricted to, water or air.

The nosepiece 14 and the headband 12 are attached to goggles 10, the headband 12 being of sufficient size to secure the goggles 10 to a human head adjacent the eyes, the nosepiece 14 being of sufficient size to secure the body to the nose. One skilled in the art will recognize that many other types of securing devices may be used to secure the goggles 10 to the head of a user. For example, alternative securing devices can include temple arms that extend rearwardly to hook over the ears.

Figure 3:
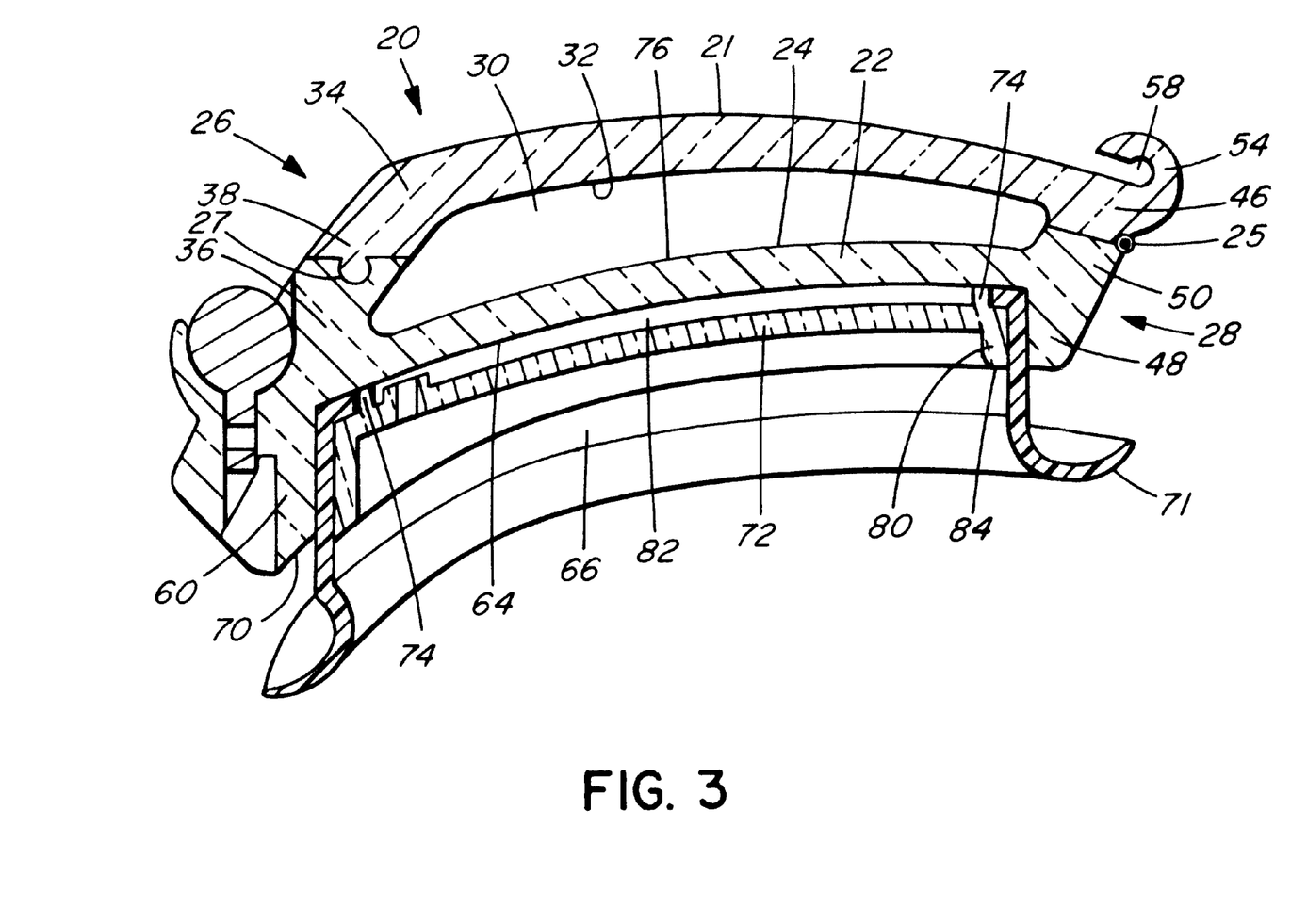
FIG. 3 is a longitudinal section view of an eyepiece according to the first embodiment taken along line 3—3 of FIG. 2b.

In the embodiment illustrated in FIG. 3, each eyepiece 20 includes first and second eyepiece side portions 26 and 28 that are spaced apart and substantially parallel to each other. The side portions 26 and 28 are connected to the anterior 21 and posterior 22 eyepiece portions and define an opening 30 extending therebetween. The body opening 30 is shaped to be generally tapered towards the second eyepiece side portion 28. Opening 30 has an opening sidewall 32, and is designed to permit fluid flow between the anterior and posterior eyepiece portions 21 and 22. In section, the first eyepiece side portion 26 is inclined away from the anterior body portion 21 so as to reduce the fluid drag, whereas the second eyepiece side portion 28 is inclined towards the anterior body portion 21. Both these inclinations produce a curved transparent portion 18 that advantageously has reduced hydro-dynamic drag when used for swimming. The second eyepiece side portion 28 is generally smaller than the first eyepiece side portion 26. This design takes into account the shape of the human face and allows the goggles to attain a stream-lined fit.

Referring to FIGS. 2c and 3, the first eyepiece side portion 26 includes a first distal eyepiece side portion 34 connected to the anterior portion 21 at an obtuse angle. A first proximal eyepiece side portion 36 is shaped to cooperate with the side of the head. A first intermediate eyepiece side portion 38 interconnects the first distal 34 and the first proximal eyepiece side 36 portions and is shaped to reduce fluid drag. The first intermediate side portion 38 has a curved first outer face 40 which is disposed parallel to the body opening 30 so as to direct fluid flow away from the anterior portion 21 when subjected to fluid flow towards the anterior portion.

In activities that subject the lenses to particulate matter, the anterior portion 21 is preferably hingedly attached to one of the side portions. Advantageously, this would allow the user easy access to the planar lens surface 24 to effect routine cleansing.

FIG. 3 shows such an arrangement in which a hinge 25 is formed across side portion 28 and a corresponding snap lock arrangement 27 or the like is formed in opposite side portion 26 to retain anterior portion 21 in place adjacent posterior portion 22. When cleaning of posterior portion 22 is necessary, snap lock 27 is released and the anterior portion pivoted about hinge 25 to expose posterior portion 22 for cleaning.

A first projection 42 extends outwardly from the first intermediate side portion 38 and has a first projection opening 44 disposed therein to permit placement of the headband 12.

As best illustrated in FIGS. 2a and 3, the second eyepiece side portion 28 comprises a second distal side portion 46 that is connected to the anterior portion 21 at an acute angle. A second proximal side portion 48 shaped to closely cooperate with the nose and the eye socket intersection. A second intermediate side portion 50 interconnects the second distal 46 and proximal side portion 48 and is shaped to closely cooperate with the nose and eye socket intersection. The second intermediate side portion 50 has a curved second outer face 52 which is disposed parallel to the body opening 30 so as to direct fluid flow away from the anterior portion 21 when subjected to fluid flow towards the anterior body portion. A second projection 54 extends outwardly from the second distal side portion 46 and has a second projection opening 58 disposed therein to permit placement of the nosepiece 14.

Referring to FIG. 3, a posterior annular sidewall 60 extends rearwardly from a rear edge or rim 64 of posterior portion 22. The posterior annular sidewall is shaped to define a recess 66. The posterior annular sidewall 60 has an annular sealing surface 70 that is disposed towards the eye socket. The annular sealing surface 70 being shaped to closely cooperate with the eye socket, thus forming a seal and therefore an air pocket between the eye and the posterior portion 22. To assist in the formation of a seal and improve comfort, a soft resilient flange 16 can be provided that extends rearwardly from the eye goggle to conform to the contours of the face and provide some cushioning for a more comfortable fit.

The posterior portion 22 of each eyepiece can also include a transparent anti-fogging member 72 that is attached to the posterior portion 22 and is shaped so as to be complimentary to the recess 66. The anti-fogging member 72 is manufactured from a transparent material and is shaped to fit snugly into the recess 66. The anti-fogging member 72 may be removed at regular intervals for cleansing purposes. The antifogging member 72 includes an anterior anti-fogging surface 76 having an annular anti-fogging side wall 74 that extends forwardly therefrom. When anti-fogging member 72 is positioned within recess 66, side wall 74 engages against the rear face of posterior portion 22 to space anti-fogging surface 76 and posterior portion 22 apart to define an anti-fogging chamber 82. An inert gas such as nitrogen may be disposed in the chamber, thus providing a moisture-free environment that is less prone to fogging.

A posterior annular anti-fogging sidewall 80 also extends rearwardly from the anterior anti-fogging surface 76. The posterior annular anti-fogging sidewall 80 has a posterior anti-fogging annular sealing surface 84 that is disposed towards the eye socket. The anti-fogging annular sealing surface 84 is shaped to form a continuous surface with the annular sealing surface 70, thereby permitting close cooperation with the eye socket to form an air pocket between the eye and the posterior portion 22. In order to form the air pocket, a user merely applies light pressure onto the body 18 to establish a seal against the face.

As best illustrated in FIGS. 1 and 2, a conventional, deformable flange 16 is preferably secured to the posterior portion 22 and provides a sealing surface to accommodate uneven facial surfaces. One skilled in the art will recognize that the flange 16 may be constructed of any deformable material, for example, sponge or rubber that is capable of forming a fluid tight seal. It will also be recognized that the flange 16 may be removed altogether to provide the optically transparent body that still retains the optical properties to implement aspects of the present invention.

ALTERNATIVES

The first embodiment of the goggles is shown as being adapted for swimming purposes, but it can also be used with an alternative design in which the anterior portion 21 of transparent body 20 defines a single band in which the sidewalls 26 and 28 are eliminated and a single column 100 is substituted to displace the anterior and posterior body portions apart. This arrangement may have applications in both cycling and swimming, and may be particularly useful for recreational activities in which cycling and swimming occur in series, for example, in triathlons. The posterior body portion is generally planar and therefore, behaves optically in a similar fashion to the planar surface of the swimming goggle arrangement in the first embodiment. When positioned over the eyes, the optical body allows increased hydro dynamic properties and reduced visual distortion.

Figure 7:
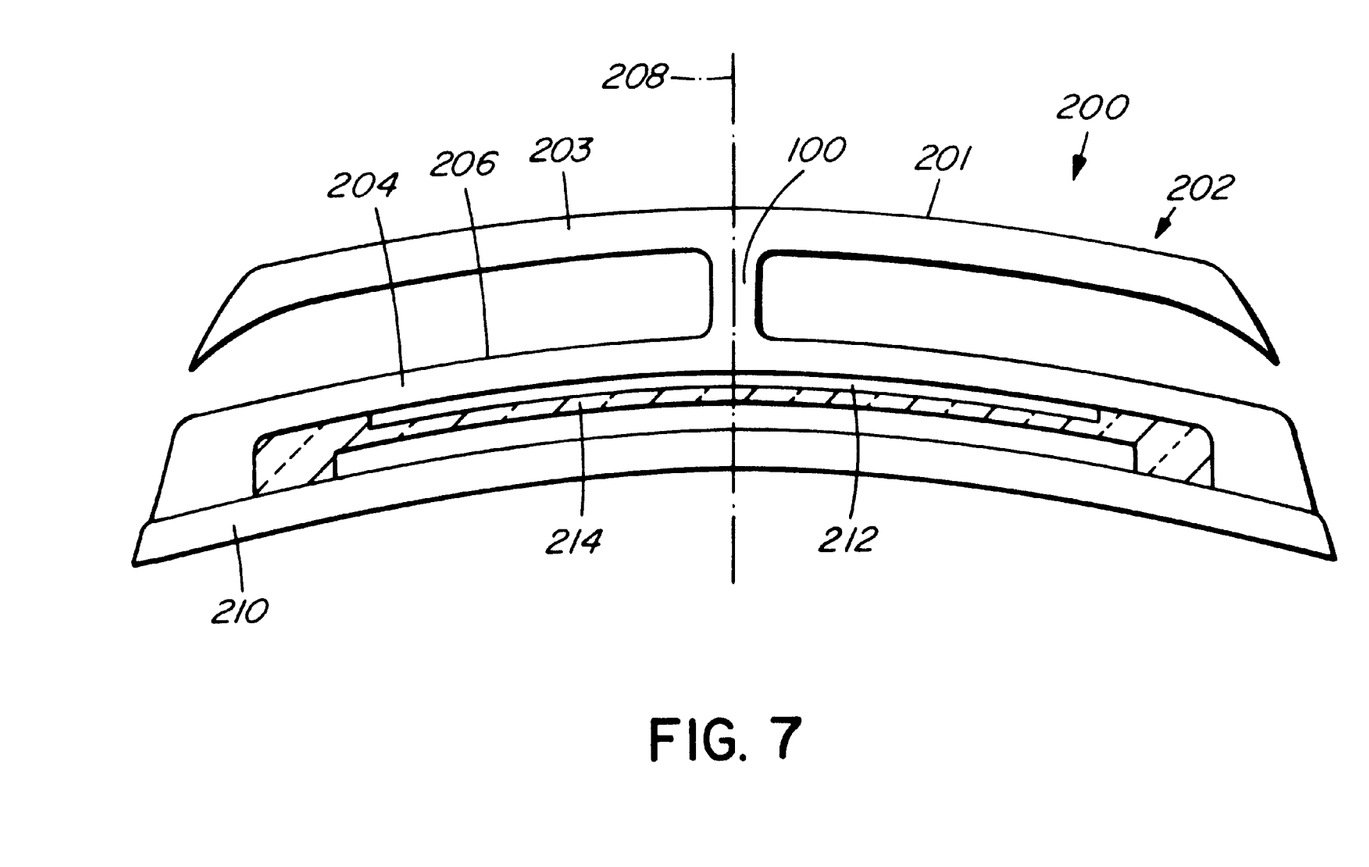
FIG. 7 is a cross-sectional view of a second embodiment of the invention showing an eyepiece in which the anterior portion is attached at single end to the posterior portion.

As best illustrated in FIG. 7, the second embodiment 200 of the invention has a transparent body 201, and eyepiece band 202 having anterior and posterior band portions 203 and 204 that are spaced apart to permit fluid flow therebetween. The anterior band portion 203 is shaped so as to reduce fluid drag and is essentially identical to the anterior portion 21 and functions identically. The posterior body band portion 204 has a substantially planar surface 206 that reduces visual distortion in essentially the same manner as that of the posterior body portion 22 of the first embodiment. In contrast to the first embodiment, the eyepiece band has a central axis 208 which disposes the anterior and posterior band portions apart. The column 100 is positioned along the axis 208 and separates the anterior and posterior band portions. The column 100 is shaped and positioned so as to allow a user an essentially unobstructed view and is positioned outwardly away from the eyes. A single face seal 210 functions in a similar fashion to the seals 16 in that an air pocket is formed upon application of pressure to the body 201 by the user. An anti-fogging recess 212 is defined by an anti-fogging member 214 and functions essentially identically to that of the first embodiment.

Figure 8:
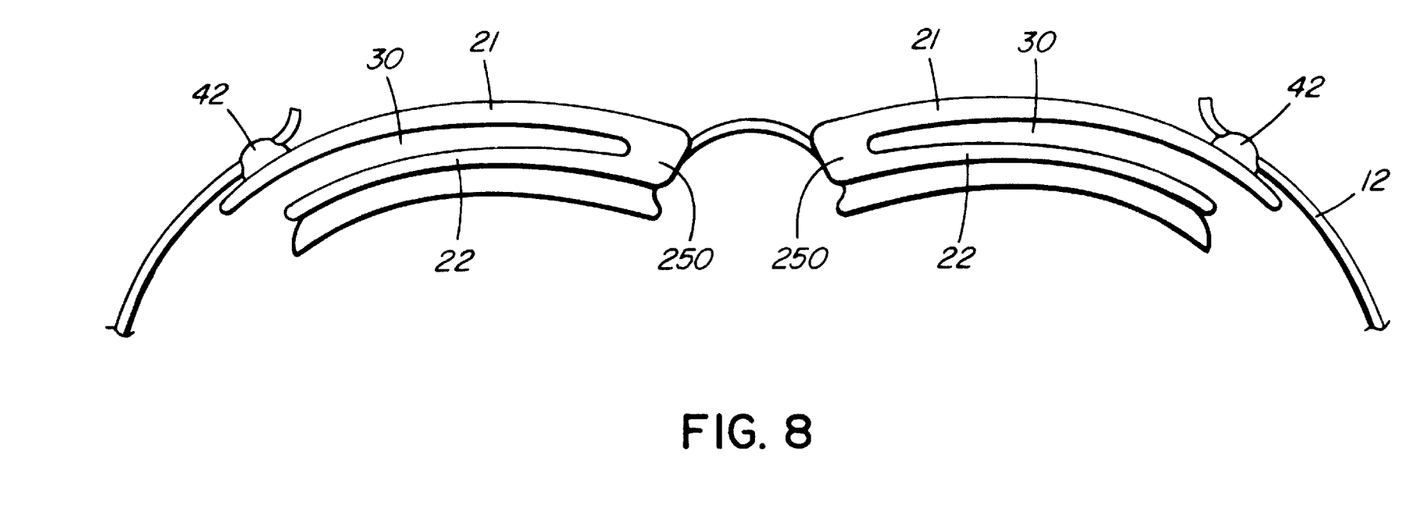
FIG. 8 is a plan view of a third embodiment of the invention.

In a still further embodiment of the present invention illustrated in FIG. 8, each eyepiece 20 is formed with an anterior portion 21 that is attached to the posterior portion 22 at a single point of attachment 250 adjacent the nose of the wearer. As in the previous embodiment, the anterior portion 21 is shaped to offer reduced drag resistance and extends across and overlaps the more planar posterior portion 22 which is shaped to provide minimal visual distortion. A gap 30 between the anterior portion and the posterior portion permits fluid to flow therebetween. Preferably, headband 12 attaches to anchor points 42 formed at the outer edges of the anterior portions.

OPERATION

Figure 4:
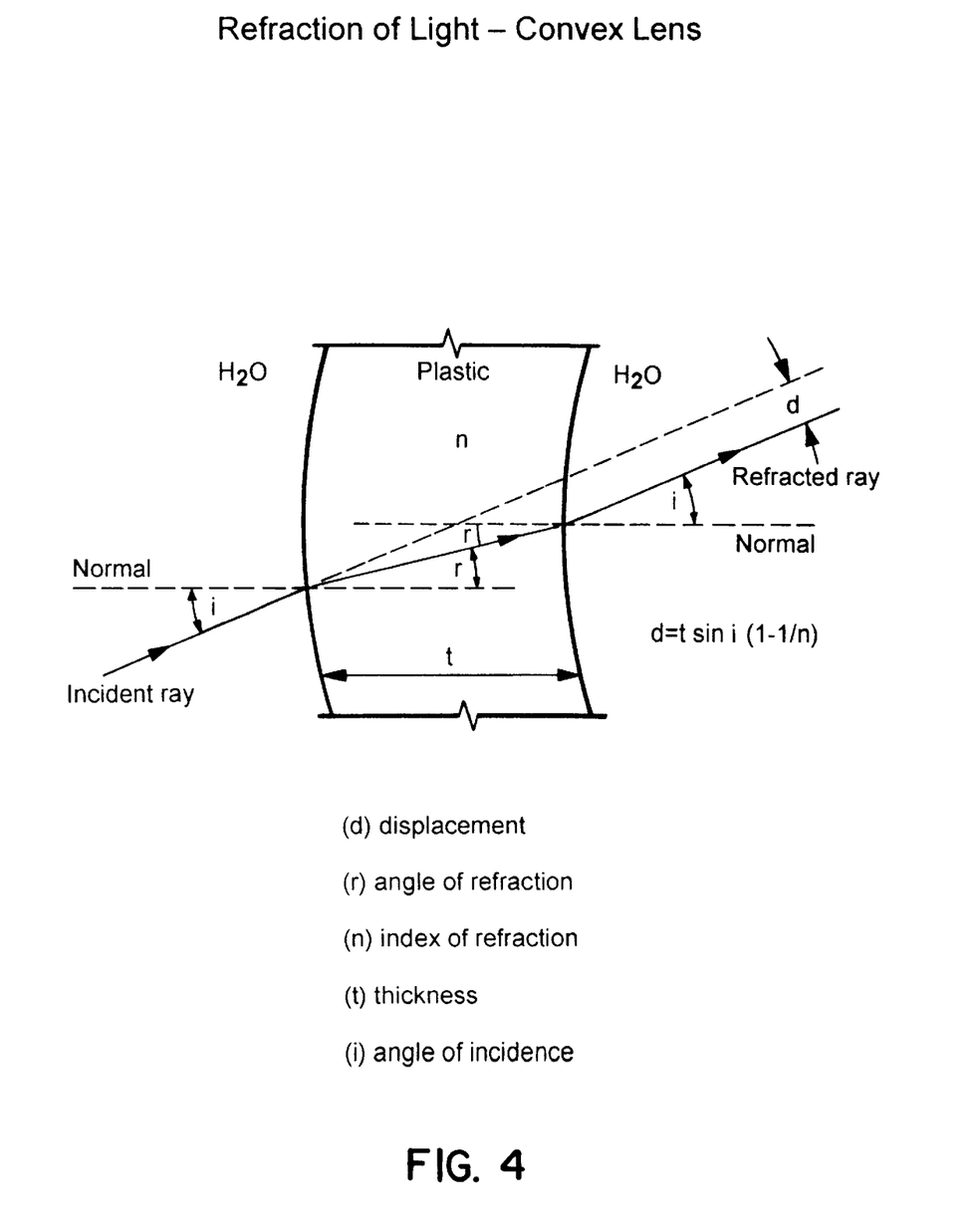
FIG. 4 is a schematic representation of light refraction across a convex lens.
Figure 5:
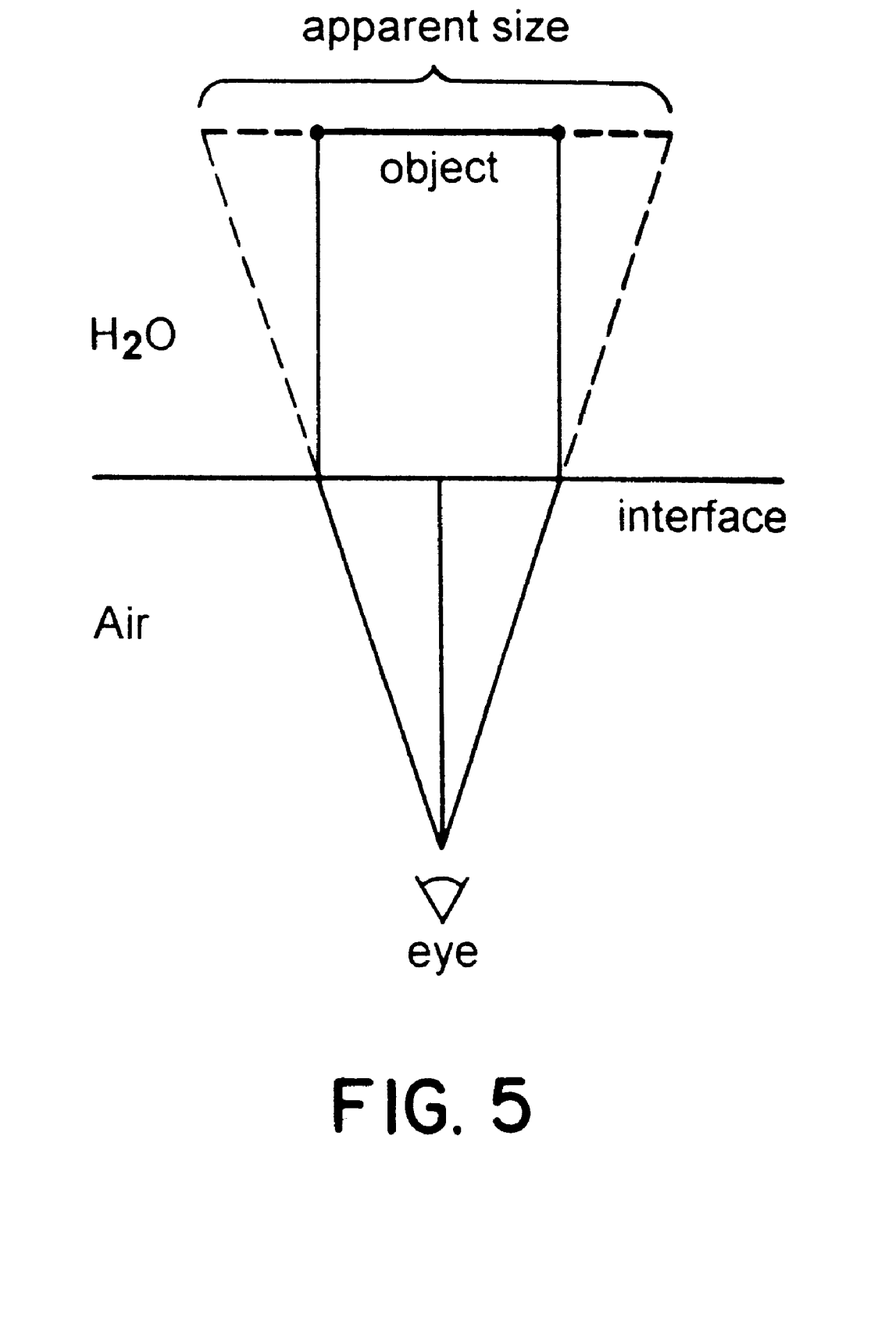
FIG. 5 is a schematic representation of refraction of light across a planar lens.
Figure 6:
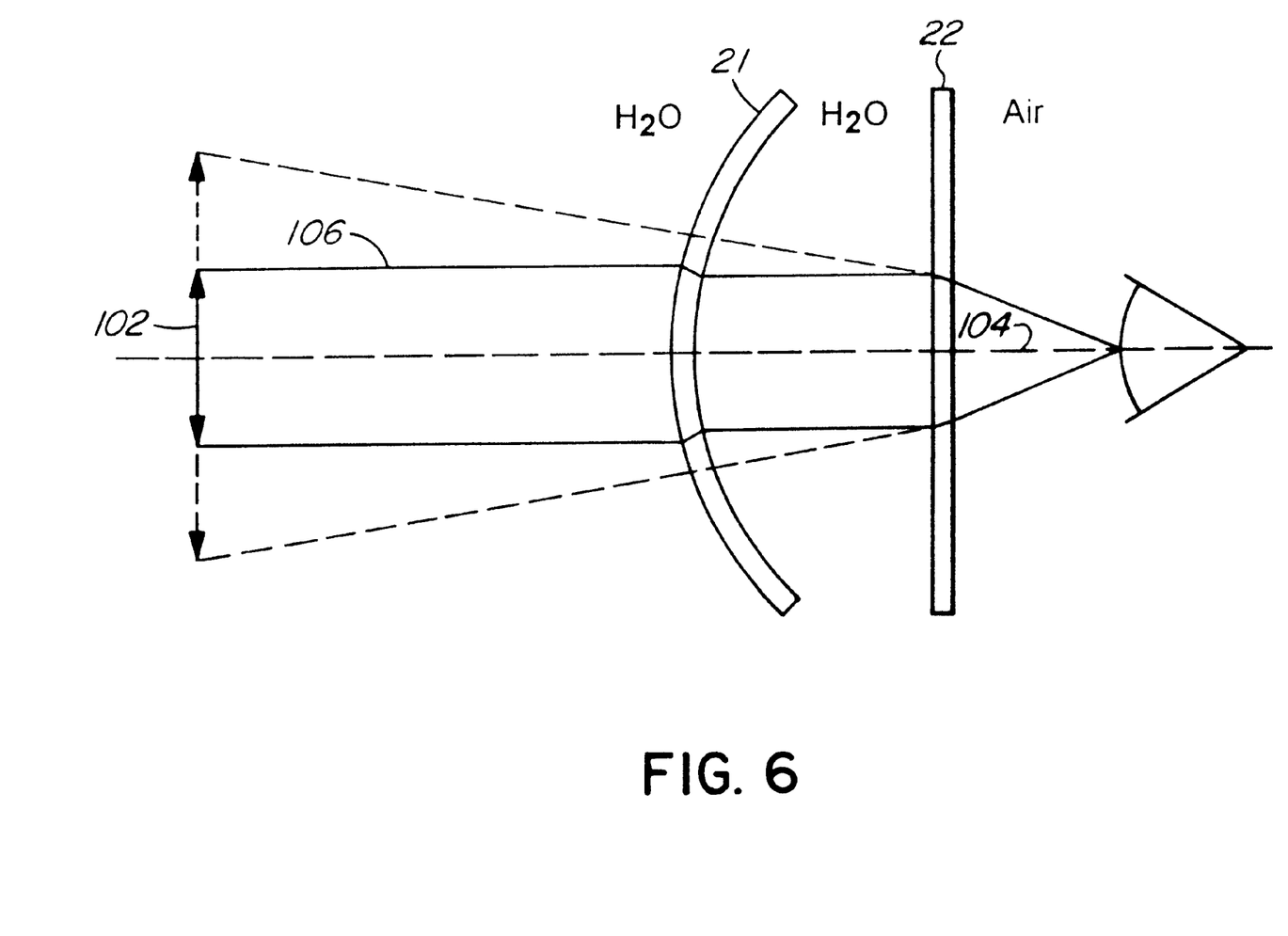
FIG. 6 is a schematic representation of the first embodiment showing light passing through the transparent anterior and posterior portions.

As illustrated in FIGS. 4 and 5, an incident light ray is refracted away from its normal path by an angle of refraction that depends upon the shape of the lens and the media through which the light ray passes. One skilled in the art will recognize that light refraction across lenses and different media causes visual distortion. As illustrated in FIG. 6, a schematic representation of the first embodiment 10 shows an object 102 positioned along an optical axis 104. A light ray 106 passes through the water medium and impinges upon the anterior body. The light ray 106 is refracted and exits the anterior body portion displaced inwardly but parallel to the optical axis. Upon reaching the flat planar surface of the posterior body portion 22, the light ray 106 is again refracted and exits the planar surface towards the eye. This refractive pathway alters the apparent size and perspective of the object as illustrated by the dotted lines and introduces distortion into the viewed image.

If the media on both sides of the lens are the same, the extent of refraction and hence visual distortion is reduced as compared to the case if different media or on each side of the lens. This is the principle on which the present invention is based. For example, the spaced anterior and posterior lens arrangement of the present invention ensures that there is water on both sides of the hydrodynamically shaped anterior lens with the result that the distortion due to the more curved anterior lens is limited to that resulting from refraction through the lens material - further distortion due to the light moving from the lens into a different medium is avoided. When light moves across the posterior lens from water to air, the posterior lens is shaped conventionally as a relatively flat, planar surface to minimize refractive distortion at the lens. The present invention is able to reduce the amount of visual distortion that one would normally expect from a curved, hydrodynamic lens by the unique arrangement of the lenses which ensures that the same medium is present on both side of the more curved lens.

While specific embodiments of the invention have been described and illustrated, such embodiments should be considered illustrative of the invention only and not as limiting the invention as construed in accordance with the accompanying claims.

We claim:

1. Goggles for use in a fluid environment comprising a transparent body adapted to be worn over the eyes having anterior and posterior body portions spaced apart to permit fluid flow therebetween, the anterior body portion being shaped so as to reduce fluid drag, and the posterior body portion being shaped to reduce visual distortion.

2. The goggles as claimed in claim 1 in which the transparent body comprises a pair of eyepieces, each eyepiece having anterior and posterior eyepiece portions adapted to be positioned over the eyes.

3. The goggles as claimed in claims 1 or 2 further comprising first and second securing portions attached to the transparent body, the first securing portion being adapted to secure the transparent body to a human head adjacent the eyes, the second securing portion being adapted to secure the transparent body to the nose.

4. The goggles as claimed in claim 2 in which each eyepiece comprises first and second eyepiece side portions spaced apart and substantially parallel to each other, the side portions joining the anterior and posterior eyepiece portions to define an opening extending between the anterior and posterior portions to permit fluid flow therebetween with the opening having sidewalls.

5. The goggles as claimed in claim 4 in which:
   (a) the first eyepiece side portion is inclined away from the anterior eyepiece portion so as to reduce the fluid drag; and
   (b) the second eyepiece side portion is inclined towards the anterior eyepiece portion, the second eyepiece side portion being smaller than the first eyepiece side portion.

6. The goggles as claimed in claim 5 in which the first eyepiece side portion comprises:

(a) a first distal eyepiece side portion connected to the anterior body portion at an obtuse angle;

(b) a first proximal eyepiece side portion shaped to cooperate with the side of the head; and (c) a first intermediate eyepiece side portion interconnecting the first distal and the first proximal eyepiece side portions and shaped to reduce fluid drag.

7. The goggles as claimed in claim 6 in which the first intermediate side portion has a curved first outer face which is disposed parallel to the body opening so as to direct fluid flow away from the anterior body portion when subjected to fluid flow towards the anterior body portion.

8. The goggles as claimed in claim 6 in which a first projection extends outwardly from the first intermediate side portion, the first projection having a first projection opening disposed therein to permit placement of the securing portion.

9. The goggles as claimed in claim 5 in which the second eyepiece side portion comprises:

(a) a second distal side portion is connected to the anterior body portion at an acute angle;

(b) a second proximal side portion shaped to closely cooperate with a nose and an eye socket intersection; and (c) a second intermediate side portion interconnecting the second distal and proximal side portions and shaped to closely cooperate with the nose and eye socket intersection.

10. The goggles as claimed in claim 9 in which the second intermediate side portion has a curved second outer face which is disposed parallel to the opening so as to direct fluid flow away from the anterior body portion when subjected to fluid flow towards the anterior body portion.

11. The goggles as claimed in claim 9 in which a second projection extends outwardly from the second distal side portion, the second projection having a second projection opening disposed therein to permit placement of a nose securing portion.

12. The goggles as claimed in claim 4 in which the opening is shaped to be generally tapered towards the second eyepiece side portion.

13. The goggles as claimed in claim 2 in which the posterior portion is a substantially flat planar lens.

14. The goggles as claimed in claim 13 in which the anterior eyepiece portion is hingeably connected to the posterior eyepiece portion.

15. The goggles as claimed in claim 2 in which the anterior portion is a smoothly curved lens extending over the posterior portion.

16. The goggles as claimed in claim 1 in which the posterior portion extends between the first and second eyepiece side portions, the posterior portion being of sufficient size and shape to substantially enclose the eye socket.

17. The goggles as claimed in claim 16 in which the posterior portion is formed with an annular sidewall that extends rearwardly from the periphery of the posterior portion, the posterior sidewall being formed with a recess.

18. The goggles as claimed in claim 17 in which the annular sidewall has an annular sealing surface disposed towards the eye socket, the annular sealing surface being shaped to co-operate with the eye socket to form an air pocket between the eye and the posterior portion.

19. The goggles as claimed in claim 18 including a transparent anti-fogging member mounted to the posterior portion, the anti-fogging member being retained in place by engagement in the recess of the posterior sidewall.

20. The goggles as claimed in claim 19 in which the anti-fogging member comprises:

(a) an anterior anti-fogging surface having an annular anti-fogging side wall extending forwardly therefrom;

(b) a posterior annular anti-fogging sidewall extending rearwardly from the anterior anti-fogging surface, the posterior annular anti-fogging sidewall being shaped to define a recess; and (c) the posterior annular anti-fogging sidewall having a posterior anti-fogging annular sealing surface disposed towards the eye socket, the anti-fogging annular sealing surface being shaped to form a continuous surface with the annular sealing surface thereby permitting close cooperation with the eye socket to form an air pocket between the eye and the posterior body portion.

21. The goggles as claimed in claim 20 in which the annular anti-fogging side wall abuts the posterior portion to define an anti-fogging chamber having an inert gas disposed therein.

22. The goggles as claimed in claim 1 further including a strip of deformable material secured to the posterior portion to provide a sealing surface to engage with the face of a wearer.

23. Swim goggles comprising:

(a) a pair of transparent eyepieces adapted to be worn over the eyes, each eyepiece having anterior and posterior portions spaced apart to permit fluid flow therebetween, the anterior portion being shaped so as to reduce fluid drag, the posterior portion being shaped to reduce visual distortion; and (b) a headband and a nosepiece attached to the eyepieces, the headband being of sufficient size to secure the swim goggles to a human head adjacent the eyes, the nosepiece being of sufficient size to secure the eyepieces over the nose.

\* \* \* \* \*